(12) United States Patent
Spickermann et al.

(10) Patent No.: US 11,324,871 B2
(45) Date of Patent: May 10, 2022

(54) BLOOD TREATMENT MACHINE

(71) Applicant: FRESENIUS MEDICAL CARE DEUTSCHLAND GMBH, Bad Homburg (DE)

(72) Inventors: Reiner Spickermann, Wasserlosen-Burghausen (DE); Pascal Kopperschmidt, Dittelbrunn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 640 days.

(21) Appl. No.: 16/097,549

(22) PCT Filed: Apr. 28, 2017

(86) PCT No.: PCT/EP2017/000547
§ 371 (c)(1),
(2) Date: Oct. 29, 2018

(87) PCT Pub. No.: WO2017/186354
PCT Pub. Date: Nov. 2, 2017

(65) Prior Publication Data
US 2019/0143025 A1 May 16, 2019

(30) Foreign Application Priority Data
Apr. 28, 2016 (DE) ...................... 10 2016 005 213.9

(51) Int. Cl.
*A61M 1/36* (2006.01)
*G16H 20/40* (2018.01)

(52) U.S. Cl.
CPC .......... *A61M 1/3656* (2014.02); *G16H 20/40* (2018.01); *A61M 2205/18* (2013.01);
(Continued)

(58) Field of Classification Search
CPC ............ A61M 1/3656; A61M 2205/18; A61M 2205/3331; A61M 2205/3344; A61M 2205/50; A61M 2205/502; G16H 20/40
See application file for complete search history.

(56) References Cited

U.S. PATENT DOCUMENTS

| 7,575,562 | B2 | 8/2009 | Oishi et al. | |
| 2006/0074369 | A1* | 4/2006 | Oishi | A61B 5/02152 604/4.01 |
| 2016/0158433 | A1* | 6/2016 | Wiktor | A61M 1/3656 604/6.09 |

FOREIGN PATENT DOCUMENTS

| CN | 1968722 | 5/2007 |
| CN | 102686251 | 9/2012 |

(Continued)

*Primary Examiner* — Philip R Wiest
(74) *Attorney, Agent, or Firm* — Jacobson Holman PLLC

(57) ABSTRACT

The present invention relates to a blood treatment machine having a control, having a pump actuator for pumping blood through an extracorporeal blood circuit which comprises an arterial line and a venous line, and having a pressure sensor for detecting the pressure in the venous line, wherein the control has a detection function for detecting a venous needle disconnect which compares a value determined on the basis of the pressure in the venous line with a limit value to recognize a venous needle disconnect, wherein the limit value with which the detection function compares the value determined on the basis of the pressure in the venous line can be set variably and/or is set variably by the control.

19 Claims, 3 Drawing Sheets

Figure 1:
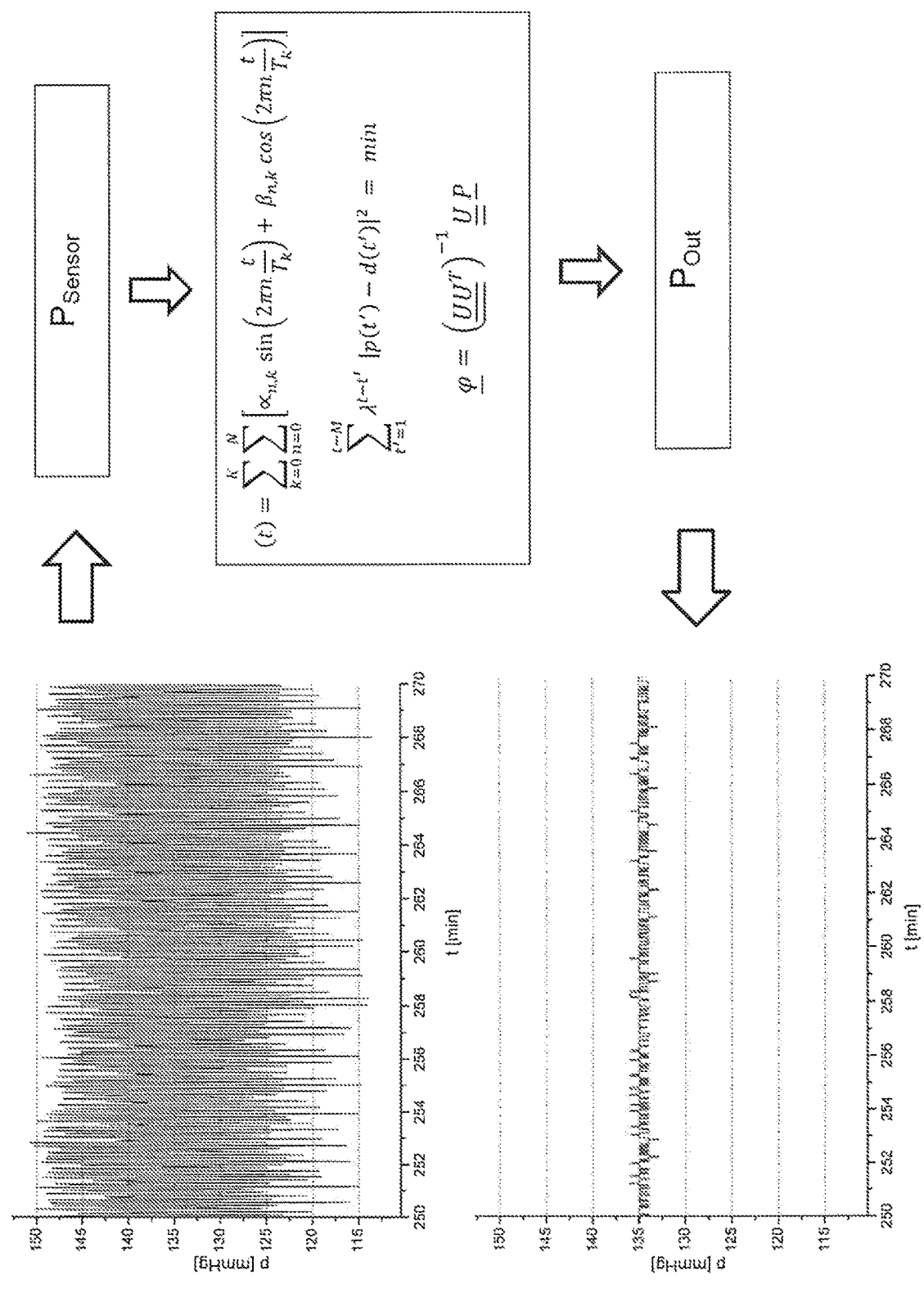

(52) U.S. Cl.
CPC ............ *A61M 2205/3331* (2013.01); *A61M 2205/3344* (2013.01); *A61M 2205/50* (2013.01); *A61M 2205/502* (2013.01)

(56) References Cited

FOREIGN PATENT DOCUMENTS

| | | |
|---|---|---|
| CN | 104 874 032 | 9/2015 |
| CN | 105517592 | 4/2016 |
| DE | 102008015832 | 10/2009 |
| DE | 102014102732 | 9/2015 |
| EP | 1815878 | 8/2007 |
| EP | 2526981 | 11/2012 |
| WO | WO 2006038396 | 4/2006 |
| WO | WO 2015/003795 | 1/2015 |
| WO | WO 2015/086384 | 6/2015 |

\* cited by examiner

BLOOD TREATMENT MACHINE

The present invention relates to a blood treatment machine having a control, having a pump actuator for pumping blood through an extracorporeal blood circuit which comprises an arterial line and a venous line, and having a pressure sensor for detecting the pressure in the venous line. It is in particular a dialysis machine in this respect.

One of the greatest risks for patients during treatment by an extracorporeal blood therapy is an unintentional disconnect of the patient needles of the extracorporeal circuit. If the arterial needle becomes loose, the pump system typically takes in air, which results in a significant change in the pressure progression on the arterial side of the extracorporeal blood circuit. As soon as this air reaches the venous air detector, it is also recognized there. The situation is therefore recognized accurately and fast as a rule.

The disconnect of the venous needle is more problematic, in contrast, since this is less easy to detect. If the arterial needle continues to remain connected, a very large blood loss arises through the open venous end when the pump keeps running. Unnoticed, this situation results in acute danger to life for the patient within a very short time.

Blood treatment machines should therefore be equipped with an alarm system which recognizes a venous needle disconnect as reliably as possible and which in this case can switch off the blood pump and block the open outlet by closing a clamp.

A plurality of recognition mechanisms are therefore already known for the disconnect of the venous needle from the prior art. In addition to other techniques, processes are frequently used in machines currently on the market which are based on a measurement of the pressure progression in the arterial line and/or the venous line. As a rule, an evaluation of the pressure values takes place in a control of the blood treatment machine to be able to draw a conclusion on the presence of a venous needle disconnect on the satisfaction of specific criteria.

The control in known blood treatment machines therefore in particular has a detection function for detecting a venous needle disconnect which compares a value determined on the basis of the pressure in the venous line with a limit value to recognize a venous needle disconnect. In this respect a change in the pressure in the venous line is typically compared with a limit value over a predefined time.

This procedure is based on the recognition that the pressure measured in the venous line of the extracorporeal blood circuit on the sliding out of the venous needle reduces within a very short time (abruptly) by the internal fistula pressure. This results from the dependence of the pressure on the flow and on the flow resistances present downstream of the pressure measurement. If marginal effects such as turbulence and the pressure-dependent expansion of the hose line are discounted, the flow resistance in the venous line built up exactly by the internal fistula pressure disappears when the venous needle slides out. The pressure measured there consequently abruptly drops by the pressure present in the fistula. The back pressure portion of the blood flow in the fistula outlet optionally also has to be taken into account.

The processes in the prior art therefore primarily monitor the signal of the venous pressure sensor with the aim of recognizing an abrupt drop of the venous pressure. A fixed value is used in known processes as a limit value for the pressure drop at which a venous needle disconnect is assumed. A value of 12, 15 or 30 mm Hg is typically used in this respect depending on the machine.

There is, however, no static pressure progression at the location of the pressure measurement in the venous line. The pressure rather undergoes a regular modulation by the peristaltic blood pump having an amplitude of typically greater than 130 mmHg. It has low-frequency noise superposed on it, influenced by different processes of the total fluidic system such as switching processes, rate changes by the substituate pump, balance chamber, ultrafiltration pump or bolus dispensing. Slower factors furthermore influence the low-frequency pressure progression such as by flow resistances in the dialyzer along the hollow fibers or transmembrane increasing due to clotting, by an increase in resistance in the clot trap or by continuous thickening of the blood due to the ultrafiltration.

The interference factors which can have an interfering influence on the recognition of a venous needle disconnect are typically greater than the reduction in the venous pressure value on an actual venous needle disconnect, partly even by several orders of magnitude. This produces an increased number of false alarms on the attempt to detect the pressure drop produced by a venous needle disconnect in a conventional manner.

To avoid frequent false alarms, the regular signal portions of the blood pump are admittedly, as shown in FIG. 1, selectively filtered in the prior art after a Fourier transform in the frequency space. This already produces a considerably smoothing of the signal in position space. Noise portions from the interference which does not occur regularly nevertheless remain, which can result in a high number of alarms triggered by false positives if a limit value is set too low. If the limit value is set too low, in contrast, the number of non-recognized needle disconnects is increased (false negatives).

Figure 2:
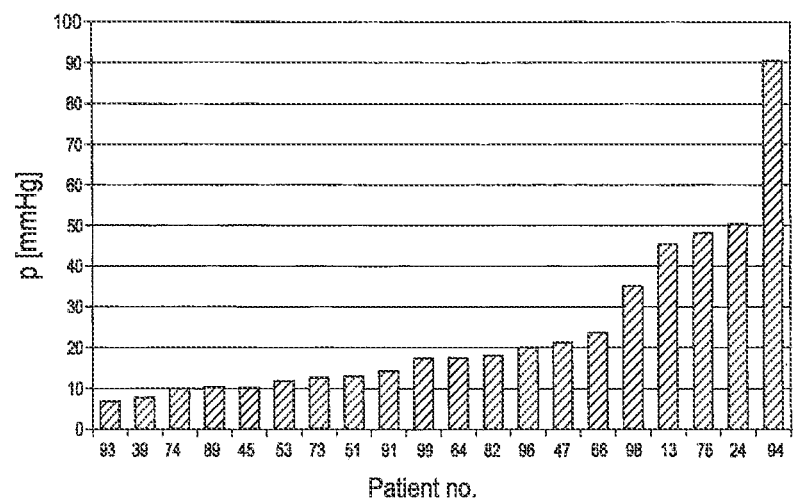

As shown in FIG. 2, however, the actual internal fistula pressure of the patients varies very substantially from patient to patient. In the collective of 20 patients shown in FIG. 2, this value fluctuates between approximately 6 mmHg and approximately 90 mmHg. If the individual internal fistula pressure is therefore below the limit value for the recognition of a venous needle disconnect, the probability is high that the detection unit does not recognize the venous needle disconnect. For this reason, the limit value in known systems is typically set very low, for example at 12 mmHg so that it is ensured that the pressure drop on a venous needle disconnect can be recognized in a plurality of the patients. However, this is at the costs of frequent false alarms.

It is therefore the object of the present invention to improve a blood treatment machine using a pressure-based detection of venous disconnects such that the number of false alarms (false positives) is decreased without reducing the sensitivity of the alarm system.

This object is achieved in accordance with the invention by a blood treatment machine having a control, having a pump actuator for pumping blood through an extracorporeal blood circuit which comprises an arterial line and a venous line, and having a pressure sensor for detecting the pressure in the venous line, wherein the control has a detection function for detecting a venous needle disconnect which compares a value determined on the basis of the pressure in the venous line with a limit value to recognize a venous needle disconnect, characterized in that the limit value with which the detection function compares the value determined on the basis of the pressure in the venous line can be set variably and/or is set variably by the control. Advantageous embodiments of the present invention are described below.

The present invention comprises a blood treatment machine having a control, having a pump actuator for pumping blood through an extracorporeal blood circuit which comprises an arterial line and a venous line, and having a pressure sensor for detecting the pressure in the venous line. The blood treatment machine can in this respect in particular be a dialysis machine, in particular for carrying out hemodialysis, hemofiltration and/or hemodiafiltration. The control has a detection function for detecting a venous needle disconnect which compares a value determined on the basis of the pressure in the venous line with a limit value to recognize a venous needle disconnect. It is now provided in accordance with the invention that the limit value with which the detection function compares the value determined on the basis of the pressure in the venous line can be set variably and/or is set variably by the control.

The present invention is in this respect based on the recognition that a venous disconnect would also still be reliably recognized with a higher limit value in patients in whom the internal fistula pressure is above the fixed limit value used in the prior art. Since the limit value can now be set variably in accordance with the invention, a higher limit value can therefore be set for such patients. The number of false alarms in this patient group is hereby reduced. A significant improvement of the treatment efficiency is thus achieved in these patients by a reduction of the false alarms without the reliability of the recognition of a venous needle disconnect being reduced. At least no worsening occurs in patients in whom the internal fistula pressure is in the region of the fixed limit values used in the prior art.

The limit value is preferably settable before the start of a treatment by the user or is set by the treatment machine before the start of a treatment. Alternatively or additionally, an adaptation of the limit value can also be possible during an ongoing treatment.

The limit value can preferably be settable and/or be set for each patient and/or for each treatment which is carried out by the blood treatment machine. The very different internal fistula pressures individual to the patients can hereby be taken into account.

The limit value can be variable by a user input in a possible embodiment of the present invention. Alternatively or additionally, the limit value can automatically be variably set by the control.

In a possible embodiment of the present invention, the detection function can determine the limit value on the basis of data which can be input into the control via an input function. They are in this respect in particular patient data which can be input into the control via the input function.

The input function can, for example, be integrated into the user interface of the treatment machine. A corresponding input prompt to input data can be provided, for example, during the start-up phase of the treatment machine, for example. Alternatively or additionally, the data can also be input via a data interface. It can, for example, be a data interface to a central data system and/or a data interface for reading out the data of a patient card. The treatment machine can in particular have a card reader, with corresponding data being stored on the patient card and being read in by the blood treatment machine.

In a further embodiment which can be combined with the last-described embodiment, the detection function can determine the limit value on the basis of data which are determined via a measurement function of the control. These are here also preferably patient data which are determined by a measurement carried out by the treatment machine.

Provision is preferably made that the measurement function determines the data with reference to measured values of a pressure sensor of the treatment machine, in particular on the basis of the measurement of the pressure in the venous line and/or arterial line. Provision can alternatively or additionally be made that a measurement routine is carried out to determine the data. The control preferably carries out the measurement routine automatically, for example before the start of the treatment and/or during the treatment.

In a possible embodiment of the present invention, the measurement function can control the pump actuator to carry out the measurement routine and can evaluate measured values of the pressure sensor in at least one predefinable operating state of the pump actuator. In this respect, the present invention makes use of the fact that the internal fistula pressure can be determined via the venous and/or arterial pressure sensor with a corresponding control of the pump actuator.

In a possible measurement routine, the pressure in the venous line and/or arterial line can be determined while the pump actuator is idle and does not pump any blood through the extracorporeal blood circuit. The present invention makes use of the fact that, with an idle pump actuator, the pressure at the venous and/or arterial pressure sensor corresponds to the internal fistula pressure of the patient, at least plus a static pressure.

In an alternative measurement routine, the pump actuator can pump blood through the extracorporeal blood circuit at two different speeds and/or pressures, with the respective pressure being determined in the venous line and/or arterial line. After the determination of the pressure in the venous line and/or arterial line at two different pump speeds or pump pressures, the measurement routine determines the pressure portion based on the internal fistula pressure by extrapolation.

A plurality of measurement routines can be implemented in the control which can be carried out together or alternatively for the determination of the data on the basis of which the limit value is set.

Independently of the question of how the data are produced on the basis of which the detection function determines the limit value, the detection function can comprise a plurality of different calculation functions for calculating the limit value from the data. A selection of the calculation function used for determining the limit value from the plurality of implemented calculation functions is preferably possible by a user input in this respect. Alternatively or additionally, the detection function can also select the respective suitable calculation function automatically using predefined criteria.

In a possible embodiment of the present invention, the limit value which the detection function uses can be directly input into the control via an input function. The limit value can hereby be directly influenced.

The detection function preferably calculates the limit value, however, on the basis of different data which can be input into the control and/or can be determined by a measurement function.

In a preferred embodiment of the present invention, the detection function calculates the limit value on the basis of the internal fistula pressure of the patient. Provision is preferably made in this respect that the detection function set the limit value higher at a higher internal fistula pressure than at a lower internal fistula pressure.

In a first variant, the internal fistula pressure can in this respect be inputtable into the control via an input function. In a second variant, the internal fistula pressure is determined via a measurement function of the control. The data on the basis of which the detection function determines the limit value, as shown in more detail above, can thus in particular be the internal fistula pressure. The input function and/or the measurement function is/are preferably configured as was already shown in more detail above.

Provision can furthermore be made that the detection function comprises a plurality of calculation functions for calculating the limit value from the internal fistula pressure. In this respect, a calculation function can be selectable from this plurality of calculation functions by a user input and/or can be selected automatically by the control using the amount of the internal fistula pressure.

The detection function preferably has at least one first calculation function which calculates the limit value in that it reduces the internal fistula pressure by a safety value. The venous pressure theoretically admittedly drops exactly by the internal fistula pressure on a venous needle disconnect. Since the limit value is selected as smaller than the internal fistula pressure by the safety value, the security of the detection of a venous needle disconnect is, however, increased.

In a first embodiment, the safety value by which the internal fistula pressure is reduced for calculating the limit value can be an absolute value, in particular a constant pressure value. The safety value can, however, alternatively also depend on the internal fistula pressure. The internal fistula pressure can, for example, be reduced by a certain factor so that the safety value makes up a specific portion of the internal fistula pressure. The safety value is in this respect, when it is an absolute value, between 2 mmHg and 20 mmHg, further preferably between 3 mmHg and 10 mmHg. If the safety value is a factor of the internal fistula pressure, it is preferably between 2% and 30%, further preferably between 5% and 20%.

The first calculation function is preferably selected when the internal fistula pressure exceeds a minimal internal fistula pressure. The control in this respect preferably checks whether the internal fistula pressure exceeds a minimal internal fistula pressure and then selects the first calculation direction or suggests it to the user.

Alternatively or additionally, the detection function can have at least one calculation function which fixes the limit value to the internal fistula pressure or to a predefined minimal value. The calculation function is in this respect preferably used at particularly low values for the internal fistula pressure. The second calculation function is preferably selected when the internal fistula pressure falls below a minimal internal fistula pressure. The control in this respect preferably checks whether the internal fistula pressure falls below a minimal internal fistula pressure and then selects the second calculation direction or suggests it to the user.

The choice of the calculation function can furthermore also be dependent on the flow in the arterial and/or venous blood line in addition to the internal fistula pressure.

It is ensured by the use of different calculation functions and thus of different forms in dependence on the internal fistula pressure of the patient that the sensitivity of the system is not unnecessarily reduced at correspondingly high internal fistula pressures. Conversely, the risk of false alarms should be reduced at low internal fistula pressures.

The minimal internal fistula pressure can in this respect be in a range between 8 and 40 mmHg, preferably in a range between 10 and 35 mmHg, further preferably in a range between 10 and 20 mmHg.

Provision can further additionally or alternatively be made that the detection function initiates an information output for the case that the internal fistula pressure falls below a minimal internal fistula pressure. The detection function in this respect in particular checks whether the internal fistula pressure falls below a minimal internal fistula pressure. If this is the case, the control outputs corresponding information to the user. The attention of the user can in this respect in particular be drawn to the fact that the possibilities for an automatic recognition of a venous needle disconnect are limited. The information output can therefore in particular be a warning.

The detection function in accordance with the invention is preferably configured such that control stops the pump actuator and/or blocks the venous line and/or triggers an alarm for the case that the value determined on the basis of the pressure in the venous line exceeds the limit value.

The value determined on the basis of the pressure in the venous line is further preferably a reduction of the pressure in the venous line over a predefined time interval. The detection function thus constantly determines the reduction of the pressure in the venous line over a predefined time interval and compares this pressure drop with the limit value. The predefined time interval can in this respect, for example, be an interval between 5 and 30 seconds, further preferably between 10 and 20 seconds. If the venous pressure decreases by more than the limit value within such a time interval, the detection function interprets this as a venous needle disconnect.

The detection function is preferably configured such that the measured signal of the pressure sensor is filtered for determining the pressure in the venous line. Periodic signal portions can in particular be filtered in this respect. The signal portions produced by the pump actuator can in particular be filtered in this respect. A transformation into the frequency space and a selective filter preferably take place for this purpose.

The blood treatment machine is preferably configured such that a extracorporeal circuit configured as a disposable can be coupled to the blood treatment machine. The extracorporeal circuit is in this respect in particular couplable to the pump actuator and to the pressure sensor. The components which come directly into contact with the blood can hereby be replaced for every treatment.

In addition to the blood treatment machine, the present invention furthermore comprises an apparatus for treating blood having a blood treatment machine in accordance with the invention, such as was described above, and having an extracorporeal blood circuit. The extracorporeal blood circuit is in this respect preferably configured as a disposable and is coupled to the blood treatment machine and in particular to the pump actuator and to the pressure sensor.

The extracorporeal blood circuit typically comprises, in addition to the venous line and the arterial line, a blood treatment element, in particular a dialysis filter and/or a hemofilter. The blood circuit configured as a disposable can be a blood bag kit. The extracorporeal blood circuit can furthermore comprise a cassette to which the venous line and the arterial line are coupled.

The present invention furthermore comprises an apparatus for detecting a venous needle disconnect during a blood treatment. The apparatus has a control having a detection function for detecting a venous needle disconnect which compares a value determined on the basis of the pressure in the venous line with a limit value to recognize a venous needle disconnect. In accordance with the invention, the limit value with which the detection function compares the value determined on the basis of the pressure of the venous line is variable in this respect.

The apparatus for detecting a venous needle disconnect and in particular the detection function is preferably configured in this respect such as was already shown in more detail above with respect to the detection function or to the control of the blood treatment machine in accordance with the invention.

Such an apparatus for detecting a venous needle disconnect can be configured as a device separate from the blood treatment machine to detect a venous needle disconnect during a blood treatment. The apparatus is, however, preferably integrated in the blood treatment machine.

The present invention furthermore comprises a method for operating a blood treatment machine or for operating an apparatus such as was described above. Provision is made in accordance with the invention in this respect that the limit value with which the detection function compares the value determined on the basis of the pressure in the venous line is set individually per patient. The setting in this respect preferably takes place on the basis of the internal fistula pressure of the patient. The limit value is in this respect preferably set higher at a higher internal fistula pressure than at a lower internal fistula pressure.

In this respect, the internal fistula pressure is preferably measured, for example by the physician or by the blood treatment machine or by the apparatus, and the limit value can be set on the basis of the internal fistula pressure individually per patient.

The limit value is in this respect preferably set before the start of a blood treatment and/or during a blood treatment.

The method in this respect preferably takes place such as was already described in more detail above with respect to the blood treatment machine in accordance with the invention and to the apparatus in accordance with the invention. The limit value is in this respect further preferably set such as was described above by the method in accordance with the invention in a blood treatment machine or apparatus.

Embodiments of the present invention will now be described in more detail with reference to the Figures.

Figure 3:
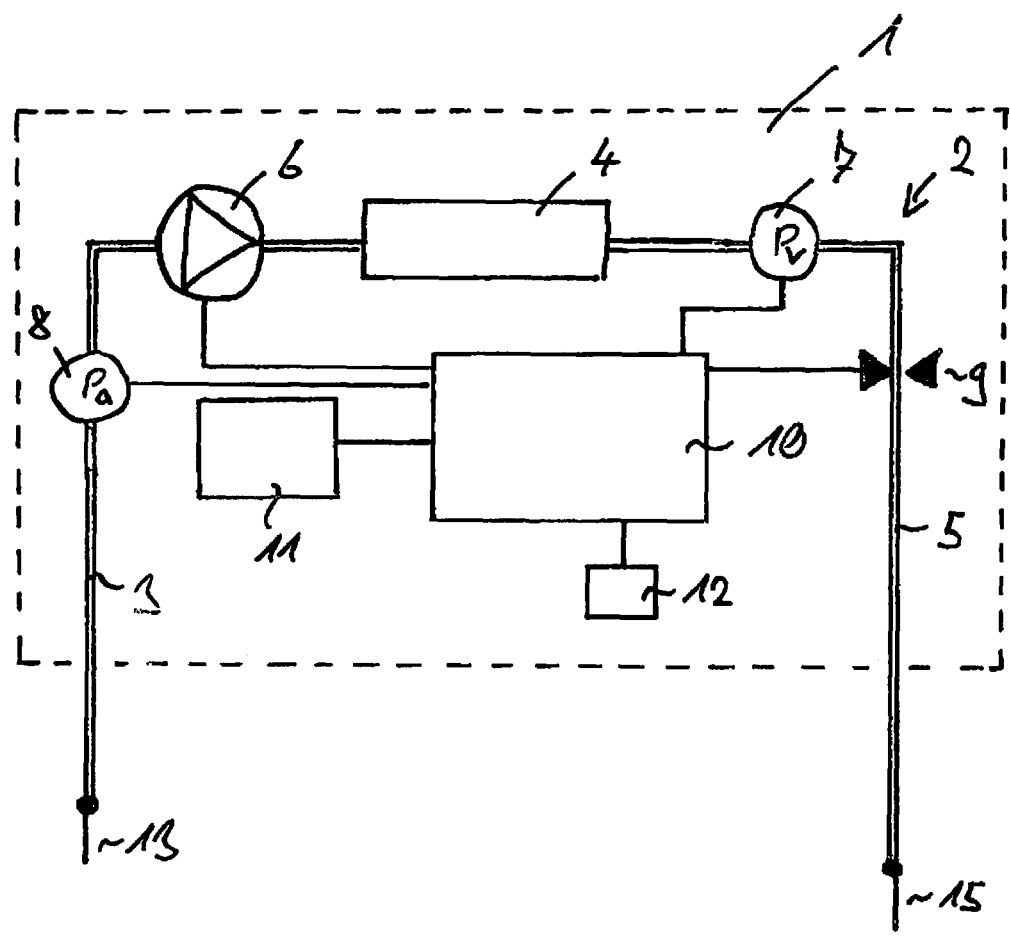

There are shown:

FIG. 1: the signal processing within a detection function in accordance with the invention, with the raw signal of the pressure sensor being shown at the top and the filtered pressure signal at the bottom;

FIG. 2: the internal fistula pressure within an exemplary patient collective; and FIG. 3: a schematic diagram of an embodiment of a blood treatment machine in accordance with the invention with an apparatus in accordance with the invention for detecting a venous needle disconnect.

FIG. 3 shows an embodiment of a blood treatment machine 1 in accordance with the invention. In the embodiment, it is a blood treatment machine for hemodialysis, hemofiltration and/or hemodiafiltration. An extracorporeal circuit 2 having an arterial line 3 and a venous line 5 can be coupled to the blood treatment machine.

The arterial line 3 has an arterial needle 13 via which the arterial access to the patient is established. The venous line 5 has a venous needle 15 via which the venous access is established. A blood treatment element 4, in particular a dialyzer and/or a hemofilter, is provided between the arterial line 3 and the venous line 5.

The blood treatment machine 1 has a pump actuator 6 which can be coupled to the pump section of the extracorporeal blood circuit in order as a blood pump to pump blood through the extracorporeal circuit. In the embodiment, the pump section is arranged in the arterial line 3. The extracorporeal circuit furthermore has coupling points for a venous pressure sensor 7 and for an arterial pressure sensor 8 of the blood treatment machine. The coupling point for the venous pressure sensor 7 is accordingly arranged in the venous line 5, the coupling point for the arterial pressure sensor 8 in the arterial line.

The blood treatment machine furthermore has a venous clamp 9 into which the venous line 5 can be placed. The blood flow through the venous line 5 can be blocked by closing the clamp 9.

The blood treatment machine furthermore has a control 10 which is shown schematically in FIG. 3 and which controls the pump actuator 6 and the clamp 9. The control 10 is furthermore connected to the venous pressure sensor 7 and to the arterial pressure sensor 8 and evaluates their signals. The blood treatment machine furthermore has an input/output 11 unit via which data can be input into the control 10 and via which information can be displayed. It can, for example, be a touchscreen on which a user guidance for operating the blood treatment machine is implemented. Alternatively or additionally, operating elements such as keys, switches, etc. can be present. A display unit can furthermore be present. The blood treatment machine in the embodiment furthermore has a schematically shown card reader 12 which is connected to the control 10. Data can read in from a patient card via the card reader.

The blood treatment machine and the extracorporeal circuit can have still further components such as balance chambers, a substituate pump, a heparin pump, further pressure sensors, bubble traps, etc., which are not shown in more detail in FIG. 3.

The control 10 in accordance with the invention has a monitoring unit for monitoring the pressure progression of the venous pressure sensor 7. The monitoring unit comprises the detection function in accordance with the invention. The detection function in this respect monitors the pressure progression of the venous pressure sensor and, on a drop of the pressure by more than the predefined limit value within a predefined time interval, draws a conclusion on a venous needle disconnect. If a venous needle disconnect is recognized, the control stops the blood pump 6, closes the clamp 9 and triggers an alarm. The predefined time interval can lie, for example, in a range between 10 and 20 seconds.

For this purpose, the detection function first evaluates the signals of the venous and/or arterial pressure sensor. A treatment of the signals is preferably carried out for this purpose such as is shown schematically in FIG. 1. The actual measured signal $P_{Sensor}$ of the venous pressure sensor is in this respect shown at the top left in FIG. 1. It is filtered by the detection function, as shown symbolically at the right. For this purpose, the regular signal portions of the blood pump are filtered from the measured signal $P_{Sensor}$, in particular by a Fourier transform and a selective filtering in the frequency space. The smoothed signal $P_{out}$ hereby resulting in position space is shown at the bottom left in FIG. 1. As can be seen from FIG. 1, noise portions from the interference which does not occur regularly also remain in this smooth signal $P_{out}$.

The signal $P_{out}$, i.e. the measured signal of the venous pressure sensor adjusted by the regular signal portions of the blood pump is then used for detecting a venous needle disconnect. The pressure drop of this signal over a predefined time interval is in this respect compared with the limit value.

In accordance with the invention, the limit value with which the detection function compares the pressure drop is variable, i.e. it can be determined individually differently for each patient or advantageously even for every treatment of a patient. The operator guidance of the blood treatment device can in this respect be configured such that this limit value is set at the blood treatment device before the start of the treatment, for example by a corresponding prompt to input data into the blood treatment device. The setting of the limit value can furthermore take place automatically by the device. In this respect, in a combined version, the device can automatically suggest a limit value which can optionally be changed by the user.

The detection function of the blood treatment device determines the limit value in the embodiment on the basis of the actually present internal fistula pressure of the patient for whom the treatment should be carried out. This actually present internal fistula pressure can be determined externally by the physician and input into the blood treatment device or can be measured directly by the blood treatment device via a measurement function.

In this respect, the control can comprise a measurement routine by which the internal fistula pressure of a patient connected to the blood treatment machine can be measured. The determination of the internal fistula pressure in this respect takes place by evaluating the pressure measured by the venous pressure sensor 7.

In a first variant, the measurement routine can in this respect open the venous clamp 9 and can stop the blood pump. In this case, a pressure is adopted at the venous pressure sensor 7 in the extracorporeal blood circuit which corresponds to the internal fistula pressure plus the hydrostatic pressure. The internal fistula pressure can therefore be determined by measuring the pressure in the venous line with a stopped blood pump and an open venous clamp 9. In this respect, in a first variant, a compensation can take place for the hydrostatic pressure. In a second variant, such a compensation can, however, be dispensed with since it can be assumed that the hydrostatic pressure also has an effect on the venous pressure measured during the normal treatment in the same manner.

In a second variant of the measurement routine, the measurement of the venous pressure can take place in the ongoing operation of the blood pump. For this purpose, the pressure is determined at the venous pressure pick-up 7 at at least two different blood pump rates. The control then determines the internal fistula pressure by means of linear regression with an idle blood pump.

The internal fistula pressure can also be determined in the same manner with the above-describe measurement routines with reference to the arterial pressure sensor 8. In the first measurement variant, the pressure in this case has to be measured at the arterial pressure sensor 8 with a stopped blood pump 6 and an open arterial clamp.

If the blood treatment machine has a corresponding measurement function for measuring the internal fistula pressure, this is preferably carried out automatically by the control before the start of a treatment and/or on the basis of an acknowledgment and/or input of a user. After the measurement of the internal fistula pressure, the detection function preferably automatically also carries out the determination of the limit value on the basis of the internal fistula pressure. In a possible embodiment, a possibility for selecting the formula for calculating the limit value from a selection of different formulas can be provided on the user interface.

Alternatively or additionally, the user interface of the blood treatment device can be configured such that the user can input the internal fistula pressure determined externally by a physician into the blood treatment device. Alternatively or additionally, a reading in of values stored on a patient card can also be provided. The internal fistula pressure is then read out by the control when a patient introduces his patient card into the card reader 12. For the case that the internal fistula pressure is determined externally by the physician and is input into the blood treatment device, the control preferably carries out the determination of the limit value automatically. A possibility for selecting the formula for calculating the limit value from a selection of different formulas can, however, be provided on the user interface.

The detection function determines the limit value used for detecting a venous needle disconnect in the subsequent treatment on the basis of the actual internal fistula pressure of the patient which is input or measured.

In the simplest embodiment, the internal fistula pressure of the patient can be used as the limit value. The limit value is, however, preferably determined by means of a formula and/or of an algorithm from the actual internal pressure and therefore deviates therefrom at least in a specific range of the internal fistula pressure. The reliability of the detection is hereby increased and the method efficiency is increased.

The internal fistula pressure of the patient less a safety window, can, for example, be used as the limit value. The safety window can depend on the internal fistula pressure in a first variant. For example, the actual internal fistula pressure less a safety window of between 5% and 20% can be used as the limit value. Alternatively, the safety window to be subtracted can comprise a fixed absolute value, for example a value between 2 mmHg and 20 mmHg, for example 5 mmHg. Alternatively or additionally, more complex formulas can also be provided for determining the limit value.

With patients having a very low internal fistula pressure, the resulting pressure limit value can be so low for the case that the limit value is determined by a deduction of a safety window from the internal fistula pressure that the number of false alarms due to the noise greatly increases. In a further embodiment of the invention, it is therefore conceivable that different formulas can be used for determining the pressure limit value in dependence on the internal fistula pressure of the patient. These different formulas are in this respect preferably applied automatically by the control in dependence on the internal fistula pressure of the patient and/or can be selected by a user.

In this respect, a formula is preferably used in which the internal fistula pressure for determining the limit value is reduced by a safety window if the internal fistula pressure is above a minimum value. If the actual internal fistula pressure of the patient is, in contrast, below such a minimum value, a reduction of the internal fistula pressure by a safety window is omitted. The internal fistula pressure can in this respect in particular be used directly as the pressure limit value. The minimum value can, for example, be 12, 15 or 30 mmHg.

It would furthermore be conceivable that the limit value is fixed to a fixed minimal value when the actual internal fistula pressure is below the minimum value or below a second lower minimum value. It is hereby prevented for internal fistula pressures which are below the typical noise that the number of false alarms increases disproportionately.

The calculation function can furthermore also be coupled to the flow in the arterial line and/or in the venous line in addition to the internal fistula pressure.

The control preferably has a warning function which, in the event that the actual internal fistula pressure is below a specific value, for example the minimum value or the second minimum value, informs the user that the possibility for the automatic recognition of a venous need disconnect is limited with the process used.

The deficiency existing in the prior art is eliminated by the blood treatment machine in accordance with the invention or by the detection function implemented there since a significant improvement in the robustness of the detection with respect to false alarms and thus a substantially increased treatment efficiency is achieved for patients whose individual internal fistula pressure is considerably above the fixed limit values selected in the prior art. A reliable recognition of venous needle disconnects is nevertheless ensured.

The variable limit value will be fixed in a comparable range in most cases for patients whose internal fistula pressure is in the range of the limit values selected in the prior art. The improvement is admittedly typically limited here, but there is also no deterioration.

A venous needle disconnect was not able to be reliably detected as a rule in the prior art for the minority of patients whose internal fistula pressure is below the fixed limit values selected in the prior art. A certain improvement may be achieved here by the present invention. An improvement in the detection of venous needle disconnect for this patient group is, however, not the focus of the present invention. Unlike the prior art, however, a warning that the possibilities for the automatic restriction of a venous needle disconnect are restricted with the method used can, however, at least be output for this patient group in accordance with the invention.

The invention claimed is:

1. A blood treatment machine having a control, having a pump actuator for pumping blood through an extracorporeal blood circuit which comprises an arterial line and a venous line, and having a pressure sensor for detecting the pressure in the venous line, wherein the control has a detection function for detecting a venous needle disconnect which compares a value determined on the basis of the pressure in the venous line with a limit value to recognize a venous needle disconnect, characterized in that the limit value with which the detection function compares the value determined on the basis of the pressure in the venous line can be set variably and/or is set variably by the control, wherein the detection function calculates the limit value individually per patient on the basis of an internal fistula pressure of the patient.

2. A blood treatment machine in accordance with claim 1, wherein the limit value can be set and/or is set before the start of the treatment and/or during the treatment; and/or wherein the limit value can be set and/or is set for each patient and/or for each treatment which is carried out by the blood treatment machine, with the limit value being variable by a user input and/or automatically being set variably by the control.

3. A blood treatment machine in accordance with claim 1, wherein the detection function determines the limit value on the basis of patient data, which can be input into the control via an input function and/or on the basis of patient data, which are determined via a measurement function of the control; and/or wherein the detection function comprises different calculation functions for calculating the limit value from the data, with a selection of the calculation function being possible by an input and/or with the detection function automatically selecting the calculation function with reference to predefined criteria.

4. A blood treatment machine in accordance with claim 3, wherein the input function is integrated into the user interface of the treatment machine and/or is provided via a data interface.

5. A blood treatment machine in accordance with claim 4, wherein the data interface is a data interface to a central data system and/or for reading the data of a patient card.

6. A blood treatment machine in accordance with claim 3, wherein the measurement function determines the data with reference to measured values of a pressure sensor of the blood treatment machine and/or carries out a measurement routine to determine the data.

7. A blood treatment in accordance with claim 6, wherein the measurement function controls the pump actuator to carry out the measurement routine and evaluates measured values of the pressure sensor in at least one predefined operating state of the pump actuator; and/or
   wherein the pressure is determined in the venous line and/or arterial line during the measurement routine while the pump actuator is idle and does not pump any blood through the extracorporeal blood circuit; and/or
   wherein the pump actuator pumps blood through the extracorporeal blood circuit at two different speed and/or pressures as part of the measurement routine and the respective pressure is determined in the venous line and/or arterial line.

8. A blood treatment machine in accordance with claim 1, with the detection function setting the limit value higher at a higher internal fistula pressure than at a lower internal fistula pressure; and/or wherein the internal fistula pressure can be input into the control via an input function and/or is determined via a measurement function of the control; and/or wherein the detection function comprises a plurality of calculation functions for calculating the limit value which can be selected by a user input and/or automatically with reference to the internal fistula pressure.

9. A blood treatment machine in accordance with claim 1, wherein the detection function has at least one first calculation function which calculates the limit value in that it reduces the internal fistula pressure by a safety value, with the first calculation function being selected when the internal fistula pressure exceeds a minimal internal fistula pressure;
   and/or wherein the detection function has at least one second calculation function which fixes the limit value to the internal fistula pressure or to a predefined minimal value, with the second calculation function being selected when the internal fistula pressure falls below a minimal internal fistula pressure.

10. A blood treatment machine in accordance with claim 1, wherein the detection function initiates an information output for the case that the internal fistula pressure falls below a minimal internal fistula pressure.

11. A blood treatment machine in accordance with claim 1, wherein the detection function stops the pump actuator and/or blocks the venous line and/or triggers an alarm in the event that the value determined on the basis of the pressure in the venous line exceeds the limit value.

12. A blood treatment machine in accordance with claim 1, wherein the detection function filters the measured signal of the pressure sensor for determining the pressure in the venous line.

13. A blood treatment machine in accordance with claim 12, wherein periodic signal portions are filtered.

14. A blood treatment machine in accordance with claim 1, wherein an extracorporeal circuit configured as a disposable is coupled to the blood treatment machine.

15. An apparatus for treating blood having a blood treatment machine in accordance with claim 1 coupled to an extracorporeal blood circuit.

16. An apparatus according to claim 15, wherein the extracorporeal circuit is configured as a disposable and is coupled to the blood treatment machine.

17. A blood treatment machine having a control having a pump actuator for pumping blood through an extracorporeal blood circuit which comprises an arterial line and a venous line, and having a pressure sensor for detecting the pressure in the venous line, wherein the control has a detection function for detecting a venous needle disconnect which compares a value determined on the basis of the pressure in the venous line with a limit value to recognize a venous needle disconnect, wherein the value determined on the basis of the pressure in the venous line, which is compared to the limit value, is a reduction in the pressure in the venous line over a predefined time interval, wherein the limit value with which the detection function compares the value determined on the basis of the pressure in the venous line can be set variably and/or is set variably individually per patient by the control, wherein the detection function calculates the limit value individually per patient on the basis of an internal fistula pressure of the patient.

18. An apparatus for detecting a venous needle disconnect in a blood treatment machine in accordance with claim 1, having a detection function for detecting a venous needle disconnect which compares a value determined on the basis of the pressure in the venous line with a limit value to recognize a venous needle disconnect, with the limit value with which the detection function compares the value determined on the basis of the pressure in the venous line being variable, wherein the detection function calculates the limit value individually per patient on the basis of an internal fistula pressure of the patient.

19. An apparatus according to claim 18, wherein the disposable is coupled to the pump actuator and to the pressure sensor.

* * * * *